United States Patent
Amann et al.

(10) Patent No.: US 8,636,725 B2
(45) Date of Patent: Jan. 28, 2014

(54) SURGICAL INSTRUMENT WITH IMPROVED HANDLEABILITY

(75) Inventors: Tobias Amann, Geislingen (DE);
Martina Heim, Walddorfhäslach (DE);
Ralf Kühner, Stuttgart (DE); Stefanie Schmidt, Pliezhausen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 0 days.

(21) Appl. No.: 13/372,749

(22) Filed: Feb. 14, 2012

(65) Prior Publication Data

US 2012/0220987 A1 Aug. 30, 2012

(30) Foreign Application Priority Data

Feb. 25, 2011 (EP) .................................. 11156053

(51) Int. Cl.
*A61B 17/00* (2006.01)
(52) U.S. Cl.
USPC .............................................. 606/1; 606/205
(58) Field of Classification Search
USPC ............... 606/1, 170, 174, 205–208; 600/131
See application file for complete search history.

(56) References Cited

U.S. PATENT DOCUMENTS

| | | | | |
|---|---|---|---|---|
| 4,950,273 A | * | 8/1990 | Briggs | 606/113 |
| 5,100,430 A | * | 3/1992 | Avellanet et al. | 606/205 |
| 5,372,124 A | * | 12/1994 | Takayama et al. | 600/106 |
| 5,897,417 A | * | 4/1999 | Grey | 446/125 |
| 5,984,939 A | | 11/1999 | Yoon | |
| 6,436,122 B1 | * | 8/2002 | Frank et al. | 606/208 |
| 2010/0234687 A1 | | 9/2010 | Azarbarzin et al. | |
| 2011/0065992 A1 | * | 3/2011 | Bissinger | 600/131 |

FOREIGN PATENT DOCUMENTS

| | | |
|---|---|---|
| DE | 298 04 860 U1 | 7/1999 |
| DE | 10156917 | 6/2003 |
| JP | 2009-28517 A | 2/2009 |
| JP | 2010-36039 A | 2/2010 |
| WO | WO 2010/009525 A1 | 1/2010 |

* cited by examiner

*Primary Examiner* — Sam Yao
*Assistant Examiner* — Nathan J Jenness
(74) *Attorney, Agent, or Firm* — Dickstein Shapiro LLP (57) ABSTRACT

A surgical instrument comprises a tool part and a grip part connected to each other via a ball and socket joint or other double-axis joint. The double axis joint allows the surgeon to work in a non-fatiguing, ergonomic and sensitive manner. The tool on the tool part can be activated e.g., mechanically by an actuation member. Additional actuation elements such as, e.g., electrical switches, can be arranged on the grip part to activate the tool. The transmission connection between the grip part and the tool can be achieved via rigid levers and connecting pieces or also via flexible elements (e.g., a traction cord), or rigid components with an integral hinge. To uncouple a pivoting movement of the grip part towards the tool part from an actuation of the tool, at least one joint of the transmission is arranged in the center of the joint.

10 Claims, 8 Drawing Sheets

SURGICAL INSTRUMENT WITH IMPROVED HANDLEABILITY

RELATED APPLICATIONS

This application claims priority to European patent application EP 11 156 053.8, filed on Feb. 25, 2011, the entirety of which is incorporated by reference herein.

TECHNICAL FIELD

The invention relates to a surgical instrument.

BACKGROUND

Surgical instruments are used by surgeons, for example, for the preparation, coagulation, thermofusion and/or dissection, in open surgical procedures or in laparoscopic or endoscopic procedures in order to perform the desired operations. Such an instrument has been known from German publication DE 101 56 917 A1, for example. This instrument is intended for endoscopic surgery and comprises a long shaft-like tool part, on the end of which is arranged a scissors or gripping forceps with movable components as the tool. The proximal end of the shaft is held on a housing that terminates on the underside in an immovable grip part. The immovable grip part is associated with a movable grip part. Both grip parts can be held like a scissors and be pivoted relative to each other just like a scissors, thus activating the tool held on the distal end of the shaft.

The instrument is designed for one-handed use, in which case the surgeon turns the instrument in the most diverse directions, as needed. In doing so, it may happen that the surgeon will adopt an unnatural hand position, potentially leading to premature fatigue, loss of fine motor skills or other detrimental effects.

SUMMARY

Considering this, it is an object of the embodiments of the invention to provide a surgical instrument of the afore-mentioned type, in which such disadvantages are remedied.

This object is achieved by an that is divided into a tool part and a grip part. The tool part preferably bears a longitudinal shaft thus defining a longitudinal axis, said shaft bearing on its distal end a surgical tool. This surgical tool comprises at least one tool member that can be activated. The activation of the tool member may be a movement, e.g., a pivoting movement, of said tool member, such as for example, when the tool member acts as a clamp, forceps or the like. The activation may also comprise other movements such as for example, a back and forth movement (e.g., when the tool member acts as a knife). The activation may also comprise other measures such as e.g., the application of heat or electric current or the like, or a combination of the aforementioned activation features.

The grip part comprises a holding grip and an actuation member. The latter is in operative contact with the tool member that can be activated. If the tool member that can be activated is a movable tool member, the operative contact is, for example, represented by a transmission-type connection so that the movable tool member can be moved by means of the actuation member.

The tool part and the grip part are connected with each other by a joint with at least two axes. In doing so, the two joint axes are oriented in a direction transverse to the longitudinal axis defined by the shaft. Thus, the surgeon can rotate the tool part and the grip part relative to each other such that he/she arrives at an ergonomic hand position, whenever needed. As a result, long-term, fatigue-free and sensitive operations are made possible.

Preferably, the tool part and grip part are designed to form a housing. Transmission means and other components such as switches, circuit boards and the like may be accommodated in this housing. The tool part and the grip part may consist of plastic material, for example. They may be made of a single or of multiple components.

Preferably, the grip part extends like a pistol grip from the tool part. Preferably, the first hinge axis is arranged inside the grip part, so that it extends through the first of the surgeon. The second hinge axis is preferably arranged transversely to the grip part, as well as transversely to the longitudinal axis of the shaft. In doing so, the joint axes and the longitudinal axis together can subtend an acute angle, a right angle or also an oblique angle.

At least the hinge axis, extending transversely to the grip part and transversely to the shaft, naturally has a limited range of rotation. Regarding the shaft, the grip part can be pivoted toward the shaft or away from the shaft, whereby the pivot angle is preferably at least 10 degrees, preferably more.

In principle, the hinge axis extending transversely to the shaft and located in the grip part may be configured without a limited range of rotation. Then, the surgeon has the option of turning the grip part relative to the tool part as often as desired in the same direction. However, it may also be practical to provide a limited range of rotation that is greater than 360 degrees, or also a range of rotation that is equal to or smaller than 360 degrees. The limited range of rotation facilitates the provision of transmission connections or electrical connections between the actuation member of the grip part and the tool part. It is then possible to dispense with contact-inactive, as well as contact-active, signal transmissions such as, for example, electrical slip rings, induction regulators, mechanical rotating couplings and the like. This allows a simple line-specific signal transmission, for example.

In the simplest case, the joint having at least two axes can be configured as a ball and socket joint; it comprises a joint ball and a joint socket. For example, the joint ball may be associated with the grip part, and the joint socket may be associated with the tool part. A reverse arrangement is possible. The ball and socket joint defines three joint axes that are at right angles relative to each other, one of them being parallel to the longitudinal axis. This can be blocked by additional measures, for example by a transmission connection between the grip part and the tool part, said connection being rigid relative to said longitudinal axis.

Preferably, the joint balls and the joint socket are in frictional contact with each other, thus providing a certain self-inhibition of the joint. A clamping device may be provided to aid the self-inhibition. The clamping device may be a continuously acting clamping member. For example, the joint socket and/or the joint head may consist of resilient material or be biased relative to each other in radial direction by spring means. This increases the friction between the joint socket and the joint ball, so that once adjusted relative positions can be reliably maintained. Additional locking devices such as eccentric levers and the like may be provided in order to enhance the clamping action as needed.

Alternatively, the self-inhibition may be aided by a detent device. The detent device may comprise projections and recesses. The projection may be arranged on the joint ball or on the joint socket. The recesses are then arranged on the respectively other part. If the projections and recesses are small enough and are arranged closely enough together, the resultant stepwise adjustability can still satisfy ergonomic requirements. The recesses and/or the projections can be resiliently arranged or provided in radial direction. For example, they can be made in one piece with the joint ball or the joint socket. Slits provided in the joint ball or the joint socket can hold tables in position tabs that hear the projections and/or recesses and thus form resilient detent members extending in a radial direction.

The joint ball may have a passage channel that leads from the interior of the tool part into the interior of the grip part. This passage channel can accommodate one or more force transmission members that transmit the motion of the actuation member to the tool part that is to be activated. The transmission may be a lever assembly or a traction drive. The lever assembly may comprise one or more levers that are hinged together. The integral hinges may act as the articulated connection.

In an advantageous embodiment, only a single transmission member is provided for converting the actuation movement of the actuation member on the grip part into a linear actuation movement in the tool part. This results in a simple robust design. The transmission member may be a multi-member lever having a flexible section such as e.g., an integrated hinge, or a flexible traction means that is freely tensioned or moves over one or more deflecting points, or a rigid lever that is supported with only one front side on a pressure surface that is being moved by the actuation member.

To make the rotating movement of the grip part relative to the tool part possible (as described above), a ball bearing is provided when e.g., a transmission member is used. This ball bearing may be arranged in the grip part or, alternatively, in the tool part, in which case the joint ball may be arranged on the transmission member and the joint socket may be arranged on the tool part or on the grip part. Alternatively, the joint socket may also be arranged on the transmission part and the joint ball may be arranged on the tool part or on the grip part.

BRIEF DESCRIPTION OF THE DRAWINGS

Hereinafter, exemplary embodiments of the invention are explained in greater detail with reference to drawings, in which.

DETAILED DESCRIPTION

Figure 1:
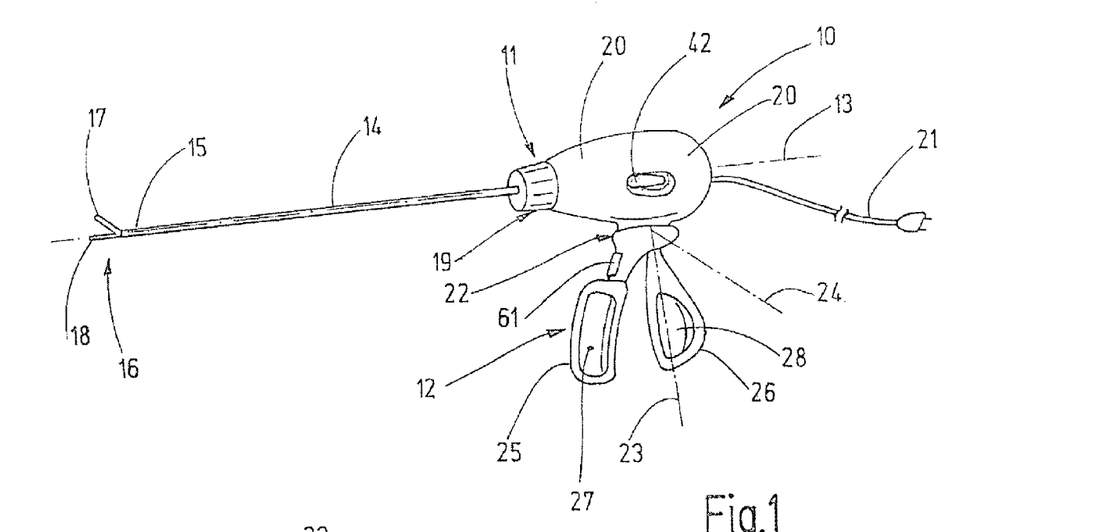
FIG. 1 is a schematized perspective representation of a surgical instrument.

FIG. 1 shows a surgical instrument 10 that is suitable for open surgery as well as for endoscopic surgery. For example, this is a multifunctional instrument for the preparation, grasping, thermofusion, coagulation and/or dissection of tissue, in particular vessels.

The instrument 10 comprises a tool part 11 and a grip part 12. The tool part 11 comprises an elongated, preferably tube-like, shaft 14 arranged along a longitudinal axis 13, said shaft bearing a tool 16 on its distal end. At least in the present example, this tool 16 comprises at least one movable tool member 17 and one additional tool member 18 that may also be movably or immovably arranged with respect to the shaft 14, as illustrated. The shaft 14 may be permanently connected or, as illustrated, may also be optionally interchangeably connected with the remaining tool part 11 via a rotating coupling 19. Due to the rotation of the shaft 14, the forceps or scissors formed by the tool members 17, 18 can be rotated about the longitudinal axis 13.

The tool part 11 further comprises a housing 20. An electrical cable 21 provided with a plug, for example, may extend from said housing 20, in which case it is possible to connect said cable 21 to a device for operating the surgical instrument 10. However, the cable 21 may also be arranged on the grip part 12.

The housing 20 is connected with the grip part 12 using at least one double-axis joint 22. Said joint 22 defines a first joint axis 23 located inside the grip part 12. The joint axis 23 is oriented in a direction transverse to the longitudinal axis 13 and subtends a right angle, or also another acute angle or oblique angle, with said longitudinal axis.

The joint 22 also defines a second joint axis 24 that is oriented in a direction transverse to the first joint axis 23, as well as transverse to the longitudinal axis 13. The angle between the joint axes 23, 24 may be a right angle, an acute angle or an oblique angle. The same applies to the angle between the joint axis 24 and the longitudinal axis 13.

The grip part 12 comprises a holding grip 25 that is rigidly mounted to the grip part 12 and a holding grip 25 that can be pivoted relative to the actuation member 26. The holding grip 25 may have a large grip opening 27 through which fit (all of) the fingers of one hand. Preferably, the actuation member 26 is provided with an opening 28 through which fits the thumb of the surgeon. However, the arrangement may also be reversed (i.e., regarding the movability and also the openings of the grip parts).

Figure 2:
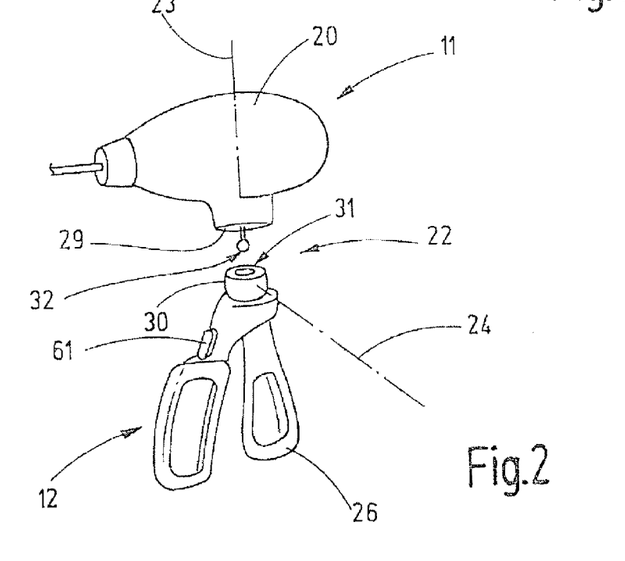
FIG. 2 is a schematized perspective representation of the surgical instrument of FIG. 1, with the grip part separated from the tool part.

FIG. 2 shows the tool part 11 and the grip part 12 separated from each other, as well as the joint 22 located in between. The housing 20 is associated with a joint socket 29. The grip part 12 is associated with a joint ball 30. Both fit so as to be easily snapped together, so that they can be moved relative to each other with moderate manual force and maintain their once assumed rotational position. The joint ball 30 can be rotated in the joint socket 29 as well as about the first axis 23 and also about the second axis 24. The joint ball 30 contains, for example, a cylindrical passage channel 31 for the accommodation of at least one force transmission member 32 that is disposed, for example, to transmit the motion of the actuation member 26 to the movable tool member 17 via a transmission.

Figure 3:
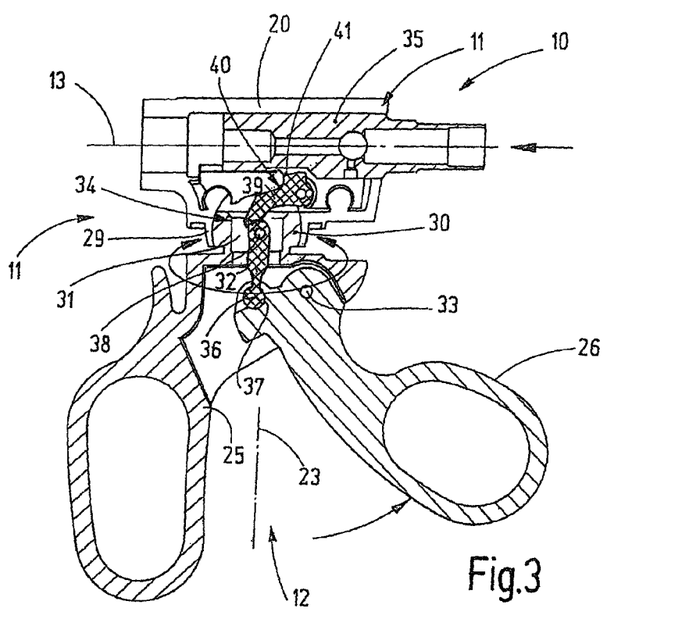
FIGS. 3 and 4 are sectional views of details of a first embodiment of the surgical instrument, with the grip part in center position in two different actuation positions.

FIG. 3 shows a vertical section of the instrument 10 and thus illustrates the internal structure of the tool part 11 and the grip part 12. As may be appreciated, the actuation member 26 is pivotally supported on the holding grip 25 by e.g., a pin 33. The pivot axis may be approximately parallel to the second joint axis 24.

Via a transmission 34, the pivoting motion of the actuation member 26 is converted into a translatory motion of a slide 35 that is movably supported in the housing 20 and actuates the tool 16 via a rod assembly (not specifically shown). The force transmission member 32 is associated with this transmission 34. This force transmission member 32 extends through the passage channel 31 and has a joint ball 36 on its lower end. This joint ball 36 is seated in a corresponding joint socket 37 that is provided at a short distance from the pin 33 on the actuation member 26. This ball 36 can be rotated in the joint socket 37 about the first joint axis 23 or an axis parallel thereto. Preferably, the center of the ball 36 is on the joint axis 23 or closely adjacent thereto.

Preferably, the force transmission member 32 is a straight pull pin that—in a hinge joint 38—is connected to an arm 39 of an angle lever 40. Said angle lever 40 is pivotally connected in the housing 20 of the tool part 11. Its other arm 41 is forked and in engagement with a groove of the slide 35. A pivoting movement of the angle lever 40 pushes the slide 35 along the longitudinal axis 13 toward the tool 16 or away from said tool.

The hinge joint 38 between the force transmission member 32 and the arm 39 prevents a pivoting of the tool part 11 toward the grip part 12 about an axis parallel to the axis 11. Additional mechanisms may be provided to block such a (third) pivot axis, should such an axis not be desirable. However, should such a third pivoting option be desired, the ball joint or an intermediate piece that is flexible in two directions may be provided instead of the hinge joint 38.

The instrument 10 may comprise additional components that are not described herein such as for example, one or more electrical switches 61 (FIG. 2) for activating a tool 16, for example an electrode, or locks 42 (FIG. 1) that completely or partially prevent a shifting of the slide 35 and thus an actuation of the tool 16, or similar mechanisms.

The surgical instrument 10 described so far operates as follows:

To use the instrument 10, the surgeon picks up the instrument 10 and rotates the grip part 12 into the desired position. To do so, the surgeon—as shown in FIG. 3—can rotate or pivot the tool part 11 and the grip part 12 relative to each other about the rotational axis 23. In FIG. 3, this is indicated by the rounded arrow. When the tool part 11 is rotated toward the grip part 12, the ball 36 rotates inside the joint socket 37, without causing any shifting of the slide 35. In this manner, the surgeon can rotate the shaft 14 in the most diverse directions (for example, longitudinally to his/her arm, transversely to his/her arm, etc.) without having to move his/her wrists in an unnatural manner.

Figure 4:
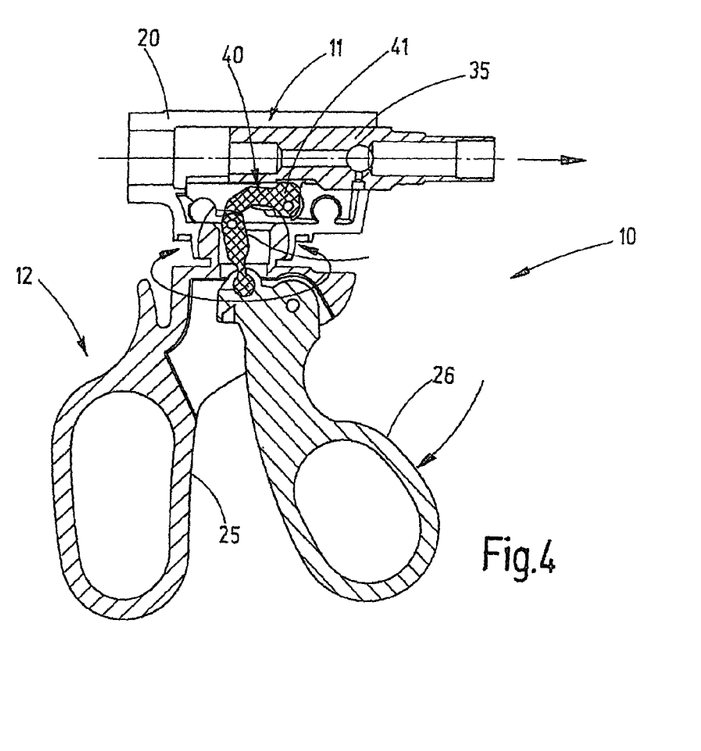
Figure 5:
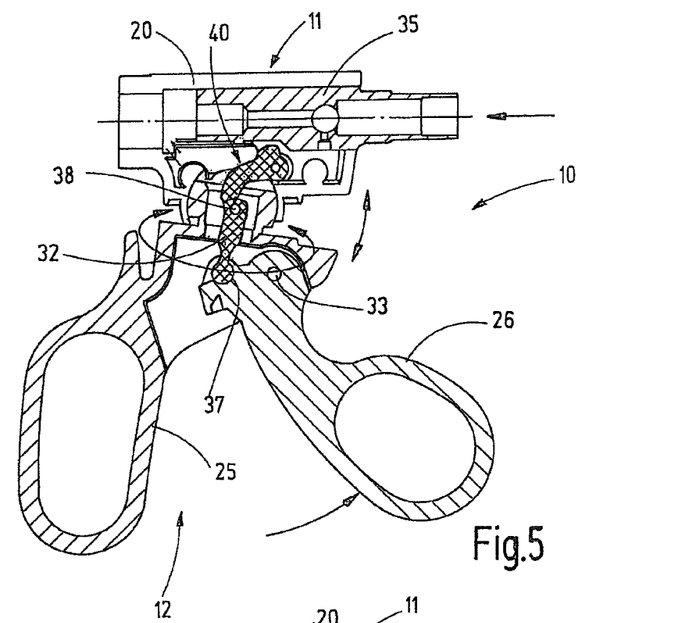
FIGS. 5 and 6 illustrate the surgical instrument of FIG. 3, with the forward pivoted grip part in two different actuation positions.
Figure 6:
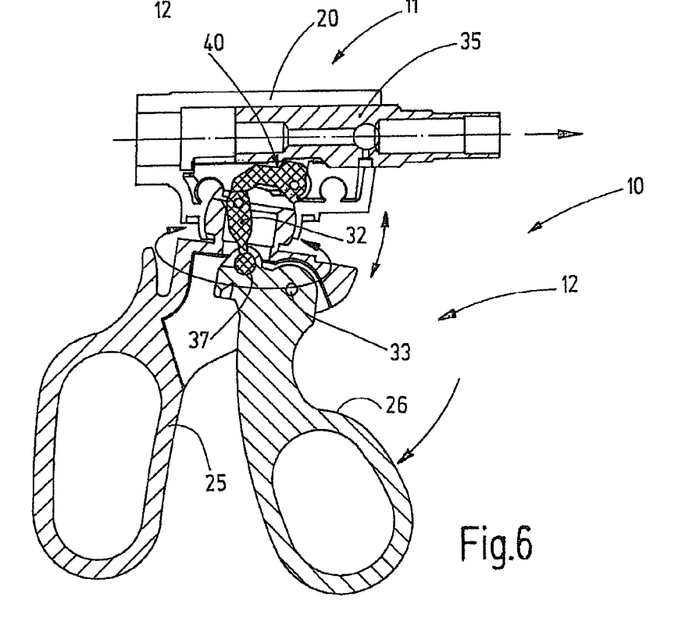
Figure 7:
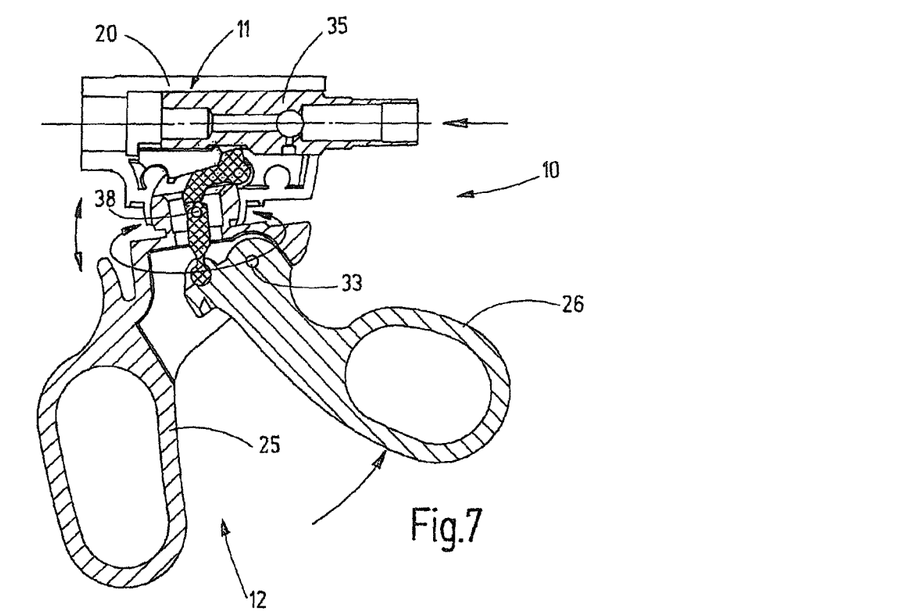
FIGS. 7 and 8 illustrate the surgical instrument of FIGS. 3 and 4, with backward pivoted grip part in two different actuation positions.
Figure 8:
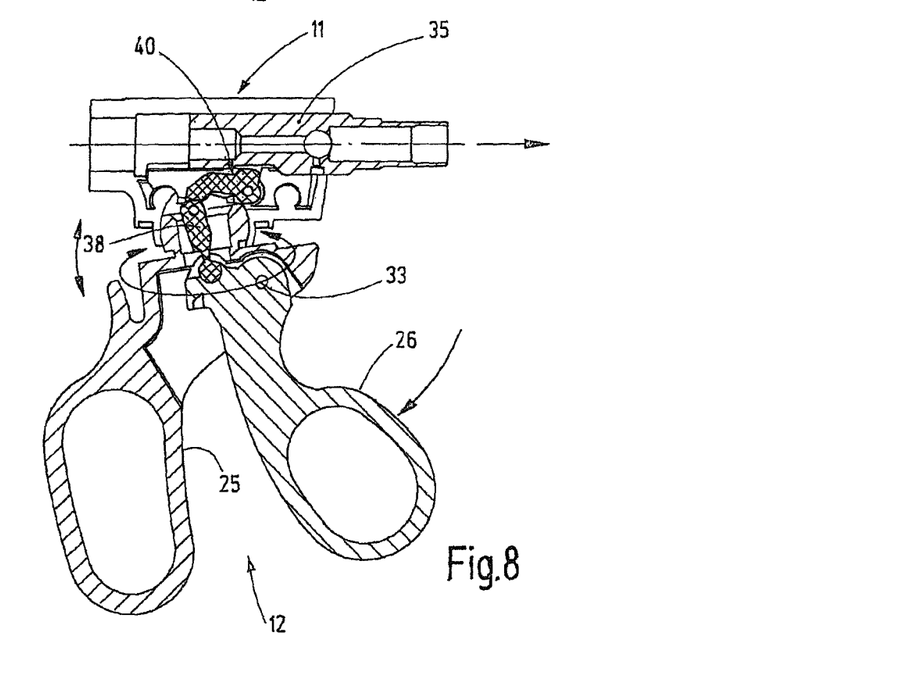

Furthermore, the surgeon can rotate the tool part 11 about the second joint axis 24 toward the grip part 12. The joint axis 24 is perpendicular in FIGS. 3 through 8. The surgeon can pivot the grip part 12 forward toward the shaft 14, as shown by FIG. 5, or backward away from the shaft 14, as shown by FIG. 7. Preferably, this pivoting motion does not result in any shifting of the slide 35. In particular, when the joint 38 is not arranged approximately in the center of the joint ball 30, as is preferred, such as when the tool 16 is not actuated. This is illustrated by FIGS. 3, 5 and 7 that show the non-actuated status in various pivot angles of the grip part 12.

In each of the pivoting positions of the grip part 12 relative to the tool part 11, it is possible to move the tool 16 in a controlled and targeted manner such that the actuation member 26 is pivoted. FIG. 4 shows this with respect to the position of the grip part 12 that is not pivoted at a right angle relative to the tool part 11. When the holding grip 25 and the actuation member 26—as indicated by the arcuate arrow—are moved toward each other, e.g., manually, the force transmission member 32 is pushed upward as a result of this. The angle lever 40 rotates clockwise and thus its arm 41 pivots the slide 35 towards the right. In doing so, a drawbar (not specifically indicated) actuates the tool 16.

The tool 16 can be actuated in the same manner when the grip part 13 is pivoted about the second joint axis 24 as in FIG. 5, e.g., toward the shaft 14 and toward the tool 16, respectively. When the actuation member 26 is pushed toward the holding grip 25 and thus pivots about the pin 33, its joint socket 37 lifts the force transmission member 32 and thus pivots the angle lever 40. This results in a shifting of the slide 35 toward the right.

The instrument 10 works in the same manner when the grip part 12 is pivoted about the joint axis 24 away from the shaft 14 or the tool 16 as in FIG. 7. In the non-actuated state, when the holding grip 25 and the actuation member 26 are at their maximum distance from each other as shown in FIG. 7, the slide 35 is in its position close to the tool (i.e., on the left side in the illustration as in FIGS. 3-8). When the actuation member 26 is pivoted toward the holding grip 25 as in FIG. 8, the force transmission member 38 is again pushed upward toward the tool part 11 causing the angle lever 40 to pivot and the slide 35 to be moved in the actuation direction (i.e., to the right in FIG. 8).

The presented ball joint coupling between the tool part 11 and the grip part 12 and the transmission 34 extending through the joint 22 allows almost any adjustment of the angle between the grip part 12 and the tool part 11, on the one hand, and an unrestricted actuation of the tool 16 in any adjusted angular position, on the other hand.

Numerous modifications of the instrument 10 described so far are possible. Hereinafter, modifications applying in particular to the transmission 34 are described as examples. These modifications of the transmission 34 described hereinafter, as well as details that can be inferred from the following description, are also applicable to above-described embodiment. The following description is restricted to modifications of the embodiment. Other than that, reference is made to the above description and the already used reference signs.

Figure 9:
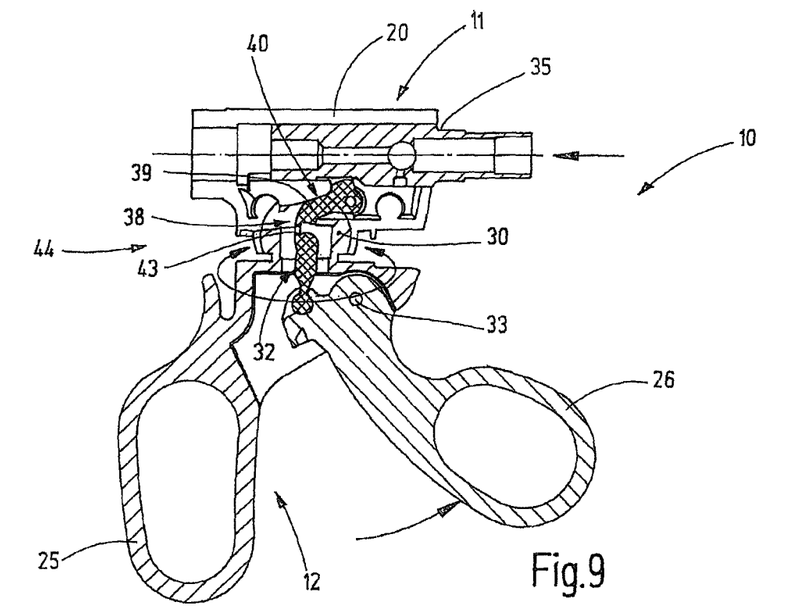
FIGS. 9 and 10 are schematized sectional views of details of an alternative embodiment of the surgical instrument in two different actuation positions.
Figure 10:
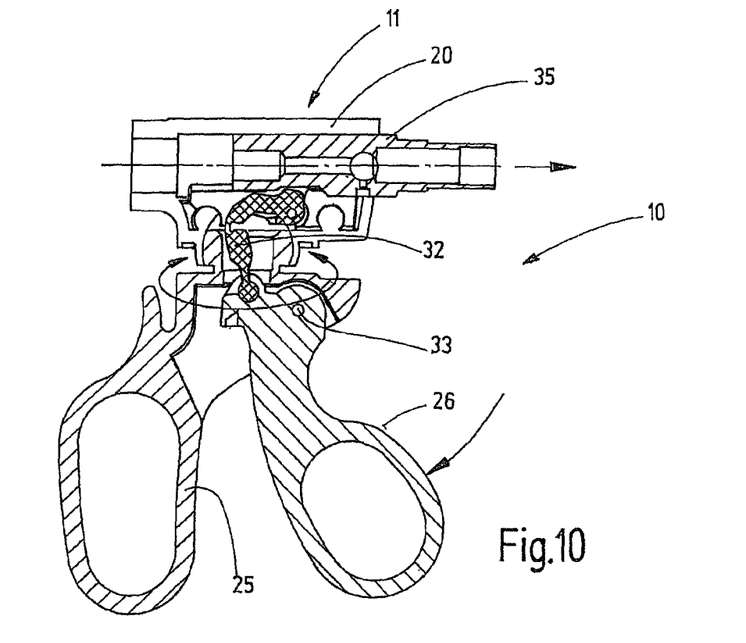

In the embodiment of FIGS. 9 and 10, the hinge joint 38 is represented by a flexible section 43 by which the plunger-like force transmission member 32 is seamlessly connected in one piece with the arm 39 of the angle lever 40. In other words, the angle lever 40 and the force transmission member 32 represent a one-piece component, i.e., preferably of plastic material, having a short thin-walled section 43 that forms, e.g., a single-axis integral hinge 44. The integral hinge 44 is preferably arranged in the center of the joint ball 30. In all rotational and angular positions of the grip part 12, the actuation is accomplished by pivoting the control part or actuation member 26 towards the holding grip 25, as shown by FIG. 10. In doing so, and as previously described, the force transmission member 32 is lifted, as a result of which the slide 35 is transferred from the left position as shown in FIG. 9 into the right position as shown in FIG. 10. The section 34 can also be configured so as to be flexible in two axes in order not to interfere with the full rotational movability of the joint 22 about three axes.

Figure 11:
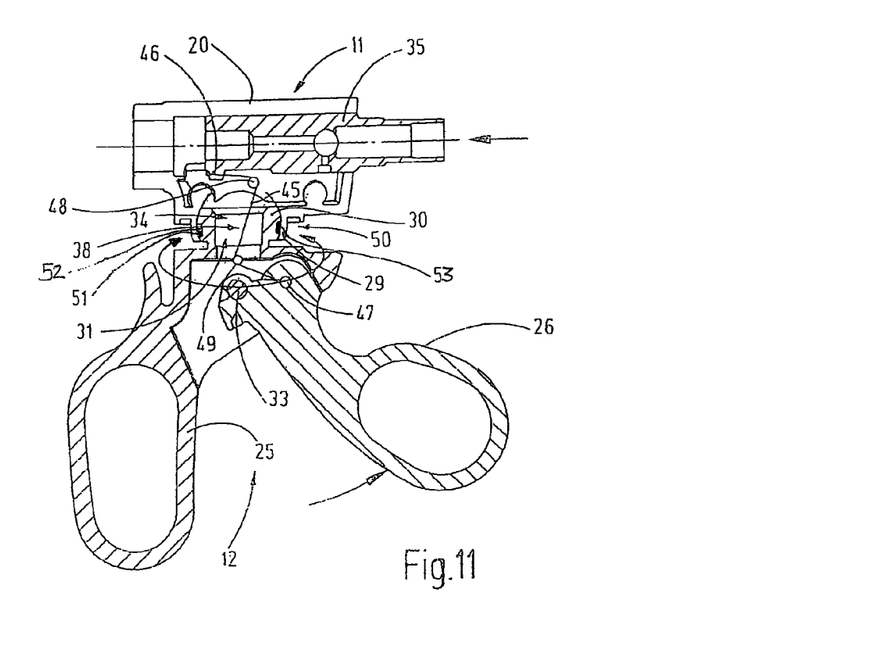
FIGS. 11 and 12 are sectional views of details of a third embodiment of the surgical instrument in two different actuation positions.
Figure 12:
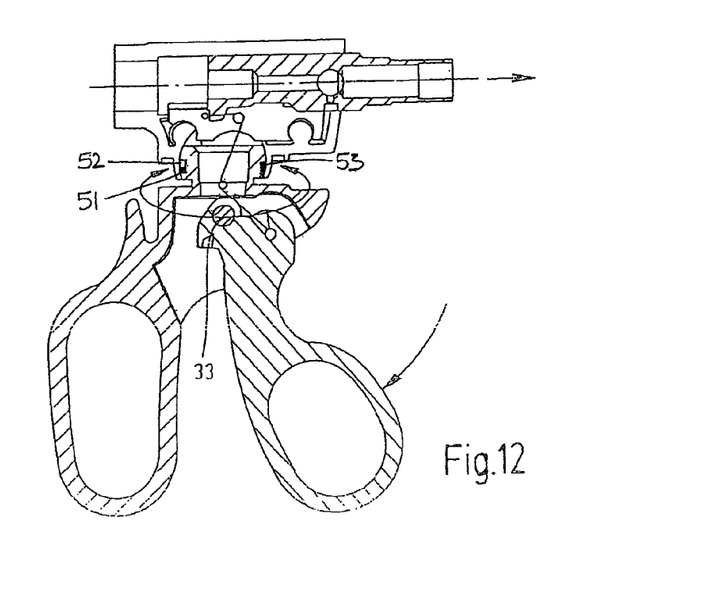

FIGS. 11 and 12 show another modification of the transmission 34. In this illustrated case, a traction mechanism 45, e.g., in the form of a thin flexible plastic line, ribbon or cord, a thin steel wire or the like is provided as the force transmission means 32. One end 46 of the traction mechanism 45 is fastened to the slide 35 and its other end is fastened to the actuation member 26. The traction mechanism 45 extends through the passage channel 31 of the joint ball 30, in which case the traction mechanism 45 may move over one or several deflecting points 48, 49 that are formed by pins, for example. The traction mechanism 45 may be provided with a rotating coupling at the two deflecting points 48, 49 in order to make the unimpaired rotation of the grip part 12 relative to the tool part 11 possible. Alternatively, the possibility of rotation about the first axis 23 may be restricted. Regarding this, FIG. 11 shows a rotation limiting mechanism 50. As such, the joint ball 30 may be provided with a peripheral groove 52 into which extends a pin 51 that may be inserted, e.g., in the joint socket 29. At one point, the peripheral groove 52 is interrupted by a wall 53 that comes into abutment with the pin 51 and thus prevents the rotation from going too far. The wall 53 shown in FIGS. 11 and 12 is exemplary, and may be at alternative locations than shown in the figures. In this way, rotational angles of less than 360 degrees can be defined. In addition, the width of the groove limits the pivot angle of the pivoting motion about the second joint axis 24.

Figure 13:
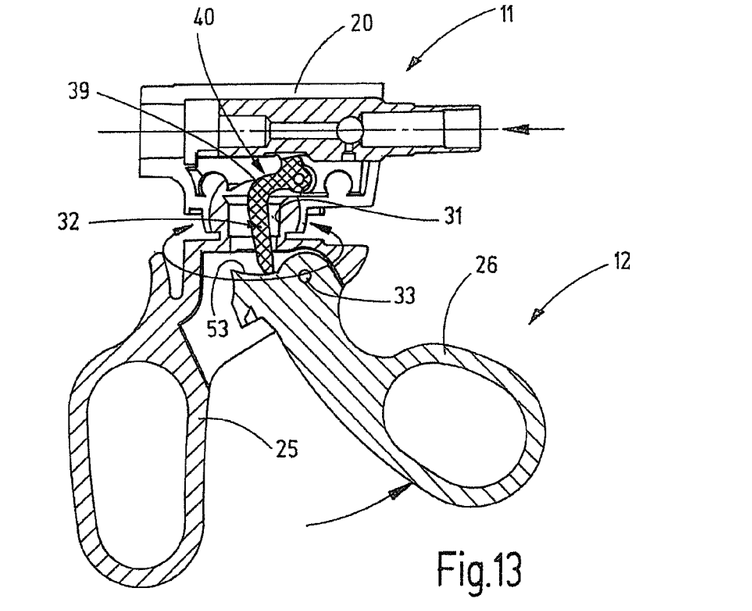
FIGS. 13 and 14 are sectional views of details of a fourth embodiment of the surgical instrument in two different actuation positions.
Figure 14:
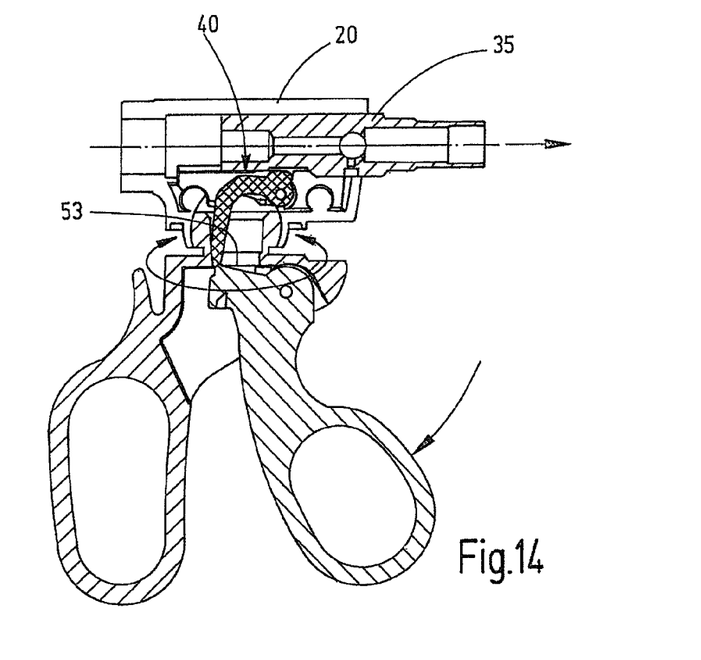

FIGS. 13 and 14 show another modification. As in the previous embodiment, it is assumed that the slide 35 is biased in the direction toward the tool 16, e.g., by a spring (not specifically illustrated). In this embodiment, the force transmission member 32 is a rigid component of the angle lever 40 and extends as a downward angled section of the arm 39 through the passage channel 31 to a spherical pressure surface 53 that is provided on a part of the actuation member 26 extending away from the pin 33 on the side of the passage channel 31. The rounded face of the force transmission member 32 is situated on this pressure surface 53. By pivoting the actuation member 26 toward the handle or holding grip 25, the pressure surface 53 is moved upward as shown in FIG. 14; as a result, the angle lever 40 is pivoted to move the slide 35 from the left (FIG. 13) to the right (FIG. 14).

Considering this embodiment, it is also possible to completely rotate and pivot the grip part 12 relative to the tool part about the two joint axes 23, 24. The tool 16 can be activated, i.e., operated in all the pivoting and rotational positions.

Figure 15:
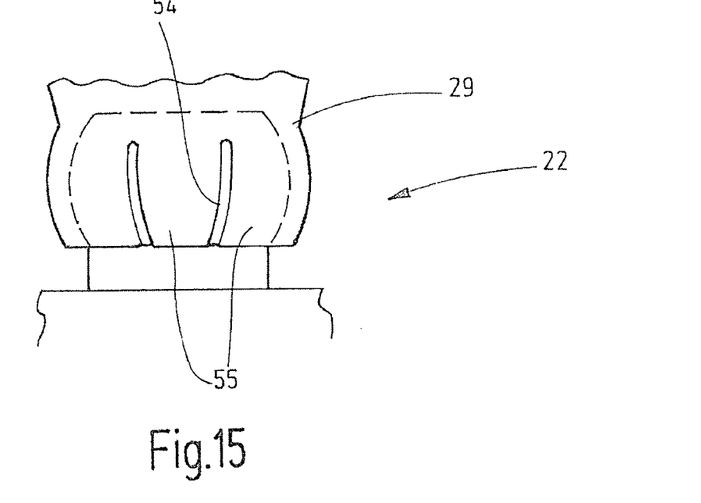
FIG. 15 is a schematized representation of a ball joint with improved clamping action.

The joint 22 of the instrument 10 may comprise frictionally engaged clamping. One relevant possible embodiment is shown in FIG. 15. The joint socket 29 can be divided into several resilient, individually separate, fingers 55 that are biased radially inward against the joint ball 30. The reverse arrangement of a joint ball with slits and a joint socket without slits is also possible.

Figure 16:
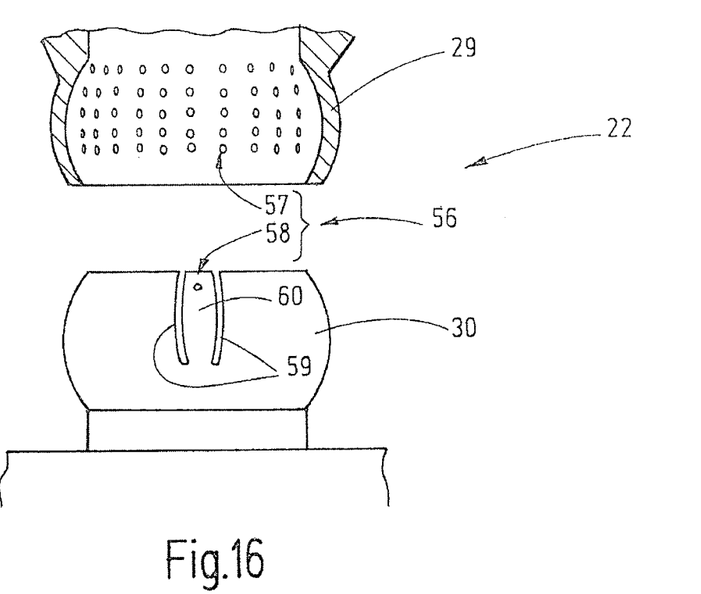
FIG. 16 is an exploded view, partially in section, of a ball joint with a detent mechanism.

Furthermore, it is possible to provide the joint 22 with a detent device 56, as is shown by FIG. 16. The detent device 56 may be associated with recesses 57 and projections 58. The recesses 57 may be provided on the inside surface of the joint socket 29 in a prespecified arrangement. This arrangement may include several rows and columns of recesses 57 that determine the desired engagement positions. The at least one projection 58 may be arranged on a tab 60 of the joint ball 30, said tab being cleared by slits 59. When the joint ball 30 and the joint socket 29 are appropriately positioned, the projection 58 snaps into a recess 57, thus securing the adopted rotational position in an engaged manner. It should be noted that, alternatively, the tab may be provided on the joint socket and the recesses on the joint ball 30.

The surgical instrument 10 in accordance with the disclosed principle comprises a tool part 11 and a grip part 12 that are connected to each other via a ball and socket joint or any other double-axis joint 22. The joint 22 allows the surgeon to work in a non-fatiguing, ergonomic and sensitive manner. The tool 16 held on the tool part 11 can be activated, for example mechanically, by the actuation member 26. Additional actuation elements such as, for example, electrical switches or the like, can be arranged on the grip part 12 to activate the tool 16, for example by supplying an electric current. The transmission connection between the grip part 12 and the tool 16 can be achieved via rigid levers and connecting pieces or also via flexible elements such as for example, a traction cord, or rigid components with an integral hinge. To uncouple a pivoting movement of the grip part 12 toward the tool part 11 from an actuation of the tool 16, at least one joint 38 of the transmission 34 is arranged in the center of the joint 22.

Details of one or more embodiments are set forth in the accompanying drawings and description. Other features, objects, and advantages will be apparent from the description, drawings, and claims. Although a number of embodiments of the invention have been described, it will be understood that various modifications can be made without departing from the scope of the invention. Also, it should also be understood that the appended drawings are not necessarily to scale, presenting a somewhat simplified representation of various features and basic principles of the invention. The invention is not intended to be limited by any portion of the disclosure and is defined only by the appended claims.

What is claimed is:
1. A surgical instrument comprising:
   a tool part comprising a shaft arranged along a longitudinal axis, and at least one activatable tool member arranged on a distal end of the shaft;
   a grip part comprising a holding grip and an actuation member;
   a joint having a passage channel through which the grip part and the tool part are connected to each other; and
   a force transmission member arranged in the passage channel
   wherein the actuation member is in operative connection with the activatable tool member via an activation mechanism located within the joint and the shaft;
   wherein the joint includes at least a first joint axis and a second joint axis,
   wherein the first joint axis is arranged to be located in the grip part and to be transverse to the longitudinal axis of the shaft and the second joint axis is arranged to be transverse to the first joint axis and to be transverse to the longitudinal axis of the shaft,
   wherein the activatable tool member is movably arranged and connected with the actuation member via a transmission, the transmission forming at least a portion of the activation mechanism,
   wherein said force transmission member is associated with the transmission and forms a portion of the activation mechanism, and
   wherein the force transmission member comprises a flexible section acting as a hinge joint, the flexible section being an integral hinge.
2. The instrument of claim 1, wherein each of the first and second joint axes comprise a rotation limiting mechanism.
3. The instrument of claim 1, wherein the transmission is a lever assembly.
4. The instrument of claim 1, wherein the joint is a ball and socket joint comprising a joint ball and a joint socket.
5. The instrument of claim 4, wherein the joint further comprises a detent device for fixing an adjusted relative position of the grip part and tool part.

6. The instrument of claim 5, wherein the detent device comprises at least one projection and at least one corresponding recess arranged on the joint ball and on the joint socket, respectively.

7. The instrument of claim 4, wherein the joint ball is connected with the grip part and the joint socket is connected with the tool part.

8. The instrument of claim 4, wherein the joint ball has the passage channel, and the passage channel connects an interior space of the tool part with an interior space of the grip part.

9. The instrument of claim 1, wherein the actuation member comprises a switch used to activate the activatable tool member.

10. The instrument of claim 1, wherein the first joint axis and the second joint axis intersect at the joint.

* * * * *